US012521225B2

(12) United States Patent
Yi et al.

(10) Patent No.: US 12,521,225 B2
(45) Date of Patent: Jan. 13, 2026

(54) MIXED-FRAME INTRALUMINAL PROSTHESIS AND METHODS THEREOF

(71) Applicant: Becton, Dickinson and Company, Franklin Lakes, NJ (US)

(72) Inventors: Peng Yi, Shanghai (CN); Zhixiu He, Shanghai (CN); Hongliang Ma, Shanghai (CN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1037 days.

(21) Appl. No.: 17/427,603

(22) PCT Filed: Jan. 31, 2019

(86) PCT No.: PCT/CN2019/074080

§ 371 (c)(1),
(2) Date: Jul. 30, 2021

(87) PCT Pub. No.: WO2020/155000

PCT Pub. Date: Aug. 6, 2020

(65) Prior Publication Data

US 2022/0117718 A1 Apr. 21, 2022

(51) Int. Cl.

*A61F 2/07* (2013.01)
*A61F 2/89* (2013.01)
(Continued)

(52) U.S. Cl.

CPC .................. *A61F 2/07* (2013.01); *A61F 2/89* (2013.01); *A61F 2/915* (2013.01);
(Continued)

(58) Field of Classification Search

CPC .... A61F 2/07; A61F 2/89; A61F 2/915; A61F 2/844

See application file for complete search history.

(56) References Cited

U.S. PATENT DOCUMENTS

| | | | |
|---|---|---|---|
| 5,246,445 | A | 9/1993 | Yachia et al. |
| 5,755,769 | A | 5/1998 | Richard et al. |

(Continued)

FOREIGN PATENT DOCUMENTS

| | | | |
|---|---|---|---|
| CN | 102488579 A | 6/2012 | |
| EP | 1302179 A2 | 4/2003 | |

(Continued)

OTHER PUBLICATIONS

PCT/CN2019/074080 filed Jan. 31, 2019 International Search Report dated Oct. 29, 2019.

*Primary Examiner* — Jerrah Edwards
*Assistant Examiner* — Aren Patel
(74) *Attorney, Agent, or Firm* — Rutan & Tucker LLP

(57) ABSTRACT

An intraluminal prosthesis (100) and methods thereof for treating at least portal hypertension. The intraluminal prosthesis (100) includes a mixed frame of a main frame (110) and a terminal frame (120), as well as a tubular graft (130) over at least the main frame (110). The main frame (110) includes a plurality of annular members (112). Each annular member (112) includes a plurality of diamond-shaped cells (114). The terminal frame (120) includes woven struts (122). The terminal frame (120) includes a coupled end (124) coupled to at least one of a first-end annular member (112*a*) or a second-end annular member (112*b*) respectively at a first end (110*a*) or a second end (110*b*) of the main frame (110). The tubular graft (130) extends from the first-end annular member (112*a*) to the second-end annular member (112*b*). The intraluminal prosthesis (100) includes an insertion state for inserting the intraluminal prosthesis (100) and an expanded state for use of the intraluminal prosthesis (100) is in use.

20 Claims, 12 Drawing Sheets

(51) Int. Cl.
*A61F 2/915* (2013.01)
*A61F 2/82* (2013.01)
*A61F 2/844* (2013.01)

(52) U.S. Cl.
CPC ... *A61F 2002/825* (2013.01); *A61F 2002/828* (2013.01); *A61F 2/844* (2013.01); *A61F 2002/91575* (2013.01); *A61F 2250/0098* (2013.01)

(56) References Cited

U.S. PATENT DOCUMENTS 5,824,037 A * 10/1998 Fogarty .................... A61F 2/07 623/1.13
5,922,019 A 7/1999 Hankh et al.
5,928,279 A 7/1999 Shannon et al.
6,001,123 A 12/1999 Lau
6,217,609 B1 4/2001 Haverkost
6,238,991 B1 * 5/2001 Suzuki ................ H01L 21/7624 257/E21.538
6,336,937 B1 1/2002 Vonesh et al.
6,348,066 B1 2/2002 Pinchuk et al.
6,350,277 B1 2/2002 Kocur
6,355,058 B1 3/2002 Pacetti et al.
6,398,803 B1 6/2002 Layne et al.
6,533,806 B1 3/2003 Sullivan et al.
RE38,091 E 4/2003 Strecker
6,673,102 B1 1/2004 Vonesh et al.
6,758,858 B2 7/2004 McCrea et al.
6,878,161 B2 4/2005 Lenker
6,899,727 B2 5/2005 Armstrong et al.
6,929,658 B1 8/2005 Freidberg et al.
7,001,425 B2 2/2006 McCullagh et al.
7,303,798 B2 12/2007 Bavaro et al.
7,399,296 B2 7/2008 Poole et al.
7,462,190 B2 12/2008 Lombardi
7,553,325 B2 6/2009 Stinson
7,753,945 B2 7/2010 Bruun et al.
7,857,844 B2 12/2010 Norton et al.
8,048,143 B2 11/2011 Shaw
8,177,832 B2 5/2012 Armstrong et al.
8,221,482 B2 7/2012 Cottone et al.
8,262,720 B2 9/2012 Bonsignore et al.
8,308,789 B2 11/2012 Armstrong
8,353,948 B2 1/2013 Besselink et al.
8,585,753 B2 11/2013 Scanlon et al.
8,694,076 B2 4/2014 Eidenschink et al.
8,721,704 B2 5/2014 Cully et al.
8,721,819 B2 5/2014 Cully et al.
8,728,611 B2 5/2014 Becher et al.
8,871,829 B2 10/2014 Gerold et al.
8,894,701 B2 11/2014 Vad
8,998,860 B2 4/2015 Sheetz et al.
9,034,034 B2 5/2015 Nitzan et al.
9,050,754 B2 6/2015 Chobotov et al.
9,061,126 B2 6/2015 Fischell et al.
9,155,491 B2 10/2015 Casanova et al.
9,402,751 B2 8/2016 Zukowski
9,427,297 B2 8/2016 Li
9,439,790 B2 9/2016 Clerc et al.
9,480,557 B2 11/2016 Pellegrini et al.
9,486,346 B2 11/2016 Argentine
9,522,072 B2 12/2016 Kovach
9,597,155 B2 3/2017 Schewe et al.
9,814,608 B2 11/2017 Clerc et al.
9,839,540 B2 12/2017 Armstrong et al.
9,907,681 B2 3/2018 Tobis et al.
9,943,399 B2 4/2018 McGhie
10,028,850 B2 * 7/2018 Tupil ........................ A61F 2/07
10,034,740 B2 7/2018 Ryan
10,070,977 B2 9/2018 Holzer et al.
10,166,128 B2 1/2019 Armstrong et al.
10,213,289 B2 2/2019 Clerc
10,219,921 B2 3/2019 Harris et al.
10,219,925 B2 3/2019 Cully et al.
10,231,838 B2 3/2019 Chin et al.
10,314,685 B2 6/2019 McMahon
10,531,941 B2 1/2020 Hynes et al.
10,603,193 B2 3/2020 Folan et al.
10,667,930 B2 6/2020 Folan et al.
10,682,220 B2 6/2020 Folan et al.
10,722,341 B2 7/2020 Binmoeller et al.
10,828,185 B2 11/2020 Armstrong et al.
10,835,397 B2 11/2020 Armstrong et al.
10,898,355 B2 1/2021 Hehrlein
10,905,539 B2 2/2021 Kovach et al.
10,933,625 B2 3/2021 Fisher et al.
10,940,299 B2 3/2021 Bareau et al.
10,952,732 B2 3/2021 Binmoeller et al.
10,973,668 B2 4/2021 Behan
11,033,411 B2 * 6/2021 Folan ........................ A61F 2/04
2002/0095205 A1 7/2002 Edwin et al.
2003/0191518 A1 * 10/2003 Spiridigliozzi ........... A61F 2/07 623/1.13
2004/0253185 A1 12/2004 Herweck et al.
2005/0137677 A1 * 6/2005 Rush ......................... A61F 2/06 623/1.13
2006/0251824 A1 11/2006 Boulais et al.
2007/0219618 A1 9/2007 Cully et al.
2008/0045896 A1 2/2008 Yribarren et al.
2008/0097404 A1 4/2008 Yribarren et al.
2009/0264990 A1 10/2009 Bruszewski et al.
2010/0004725 A1 * 1/2010 Zipse ...................... A61F 2/966 623/1.22
2011/0093002 A1 4/2011 Rucker et al.
2016/0296317 A1 10/2016 Timmermans et al.
2019/0125517 A1 * 5/2019 Cully .................. A61M 27/002
2019/0209284 A1 7/2019 Roeder et al.
2019/0247177 A1 8/2019 Kim
2019/0269498 A1 9/2019 Arbefeuille et al.
2019/0328562 A1 10/2019 Mayle et al.
2019/0388214 A1 12/2019 Silverman et al.
2020/0022828 A1 * 1/2020 Armstrong ................ A61F 2/90
2021/0015598 A1 1/2021 Folan et al.
2021/0038413 A1 2/2021 Armstrong et al.
2021/0068996 A1 3/2021 Armstrong et al.
2021/0077246 A1 3/2021 Cully et al.

FOREIGN PATENT DOCUMENTS

WO 2011082280 A1 7/2011
WO 2013184630 A1 12/2013
WO 2014067656 A1 5/2014
WO 2015179468 A1 11/2015
WO 2018144971 A1 8/2018
WO 2020155000 A1 8/2020
WO 2021086104 A1 5/2021

* cited by examiner

SECTION A-A

MIXED-FRAME INTRALUMINAL PROSTHESIS AND METHODS THEREOF

PRIORITY

This application is a U.S. national stage application of International Application No. PCT/CN2019/074080, filed Jan. 31, 2019, which is incorporated by reference in its entirety into this application.

BACKGROUND

In a healthy person, blood flowing from the stomach, esophagus, or intestines first flows through the liver. In an unhealthy person having, for example, liver damage, there can be blood flow-restricting blockages such that blood cannot easily flow through the liver. Such a condition is known as portal hypertension. Common causes of portal hypertension include alcohol abuse, blood clots in a vein that flows from the liver to the heart, too much iron in the liver (e.g., hemochromatosis), hepatitis B, or hepatitis C. When portal hypertension occurs, the blood flow-restricting blockages can elevate pressure in the portal vein causing it to rupture and seriously bleed. A person with portal hypertension can also have bleeding from the veins of the stomach, esophagus, or intestines (e.g., variceal bleeding), a buildup of fluid in the belly (e.g., ascites), or a buildup of fluid in the chest (e.g., hydrothorax). Disclosed herein is an intraluminal prosthesis and methods thereof for treating at least portal hypertension.

SUMMARY

Disclosed herein is an intraluminal prosthesis having an insertion state and an expanded state, the intraluminal prosthesis including, in some embodiments, a main frame, a terminal frame, and a tubular graft. The main frame includes a number of annular members. Each annular member includes a number of diamond-shaped cells. The terminal frame includes woven struts. The terminal frame includes a coupled end coupled to at least one of a first-end annular member or a second-end annular member respectively at a first end or a second end of the main frame. The tubular graft is over the main frame. The tubular graft extends from the first-end annular member to the second-end annular member.

In some embodiments, the terminal frame includes an uncoupled end portion opposite the coupled end. The uncoupled end portion has a diameter greater than a diameter of the main frame in the expanded state of the intraluminal prosthesis.

In some embodiments, the uncoupled end portion includes an odd number of tantalum keys capping the woven struts. The tantalum keys have a width greater than that of the woven struts to facilitate identification of the tantalum keys by radiographic methods.

In some embodiments, each annular member includes a number of ‘S’-shaped struts forming the diamond-shaped cells. Each ‘S’-shaped strut includes a cross-sectional shape bounded by two parallel arcs and two polynomial curves.

In some embodiments, any two adjacent annular members are coupled together solely by a flexible coupling provided by the tubular graft over the two adjacent annular members.

In some embodiments, the flexible coupling about the any two adjacent annular members enables the intraluminal prosthesis to keep a same length whether the intraluminal prosthesis is in the insertion state or the expanded state.

In some embodiments, the flexible coupling imparts flexibility to the main frame about the any two adjacent annular members.

In some embodiments, the tubular graft prevents tissue ingrowth about the main frame, thereby maintaining the flexibility of the main frame.

In some embodiments, the tubular graft is high-density polyethylene (“HDPE”) or expanded polytetrafluorethylene (“ePTFE”).

In some embodiments, both the main frame and the terminal frame are nitinol.

Also disclosed herein is an intraluminal prosthesis including, in some embodiments, a mixed frame of a main frame and a pair of terminal frames, as well as a tubular graft. The main frame includes a number of physically separate annular members. Each annular member includes a number of ‘S’-shaped struts forming a number of diamond-shaped cells. The pair of terminal frames includes woven struts. Each terminal frame includes a coupled end exclusively coupled to one of a first-end annular member or a second-end annular member respectively at a first end or a second end of the main frame. The tubular graft is over the main frame. The tubular graft extends from the first-end annular member to the second-end annular member.

In some embodiments, each terminal frame includes an uncoupled end portion opposite the coupled end. The uncoupled end portion includes an odd number of tantalum keys capping the woven struts. The tantalum keys have a width greater than that of the woven struts to facilitate identification of the tantalum keys by radiographic methods.

In some embodiments, any two adjacent annular members are coupled together solely by a flexible coupling provided by the tubular graft over the two adjacent annular members.

In some embodiments, the tubular graft is high-density polyethylene (“HDPE”) configured to prevent tissue ingrowth about the main frame, thereby maintaining flexibility in the main frame about the annular members.

In some embodiments, a length L of the main frame is satisfied by Equation 1:

$$L=ML_1+(M-1)S \quad \text{(Equation 1)},$$

wherein M is the number of annular members, $L_1$ is a major dimension of the diamond-shaped cells, and S is determined in accordance with Equation 2:

$$S=\sqrt{L_1^2+L_2^2}-L_1 \quad \text{(Equation 2)},$$

wherein $L_2$ is a minor dimension of the diamond-shaped cells determined in accordance with Equation 3:

$$L_2=\pi D_1/N \quad \text{(Equation 3)},$$

and wherein $D_1$ is a diameter of the main frame in an insertion state or an expanded state of the intraluminal prosthesis and N is the number of diamond-shaped cells in each annular member.

Also disclosed herein is a method for a mixed-frame intraluminal prosthesis including, in some embodiments, forming a main frame of the mixed frame by fixedly attaching a number of physically separate annular members to a tubular graft, each annular member including a number of ‘S’-shaped struts forming a number of diamond-shaped cells; forming a pair of terminal frames of the mixed frame by weaving a first set of struts to a first-end annular member at a first end of the main frame to form a first terminal frame and weaving a second set of struts to a second-end annular member at a second end of the main frame to form a second terminal frame; and fixing ends of each set of struts together with tantalum keys suitable for identification thereof by radiographic methods.

In some embodiments, the method further includes longitudinally arranging each annular member relative to a previous annular member before attachment to the tubular graft when forming the main frame, thereby ensuring flexibility of flexible couplings between the annular members provided by the tubular graft.

In some embodiments, fixedly attaching the annular members to the tubular graft includes inserting the annular members into the tubular graft before attachment to the tubular graft or sandwiching the annular members between the tubular graft and another tubular graft before attachment to either tubular graft.

In some embodiments, fixing the ends of each set of struts together with the tantalum keys includes fixing the ends of each set of struts together such that an odd number of tantalum keys result.

In some embodiments, the method further includes fixing any remaining ends of each set of struts together without the tantalum keys to satisfy the odd number of tantalum keys.

These and other features of the concepts provided herein will become more apparent to those of skill in the art in view of the accompanying drawings and following description, which disclose particular embodiments of such concepts in greater detail.

DRAWINGS

DESCRIPTION

Figure 1:
FIG. 1 illustrates an intraluminal prosthesis in a portal vein in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

In a healthy person, blood flowing from the stomach, esophagus, or intestines first flows through the liver. In an unhealthy person having, for example, liver damage, there can be blood flow-restricting blockages such that blood cannot easily flow through the liver. Such a condition is known as portal hypertension. Common causes of portal hypertension include alcohol abuse, blood clots in a vein that flows from the liver to the heart, too much iron in the liver (e.g., hemochromatosis), hepatitis B, or hepatitis C. When portal hypertension occurs, the blood flow-restricting blockages can elevate pressure in the portal vein causing it to rupture and seriously bleed. A person with portal hypertension can also have bleeding from the veins of the stomach, esophagus, or intestines (e.g., variceal bleeding), a buildup of fluid in the belly (e.g., ascites), or a buildup of fluid in the chest (e.g., hydrothorax). Disclosed herein is an intraluminal prosthesis and methods thereof for treating at least portal hypertension.

FIG. 1 illustrates an intraluminal prosthesis 100 or transjugular intrahepatic portosystemic shunt ("TIPS") 100 in a portal vein PV carrying blood to a liver L in accordance with some embodiments. The intraluminal prosthesis 100, which can be placed in the portal vein PV by a clinician in a placement procedure with a percutaneous catheter delivery system, restores patency of the portal vein PV such that blood can easily flow through the liver rather than being blocked by blood flow-restricting blockages.

Figure 2A:
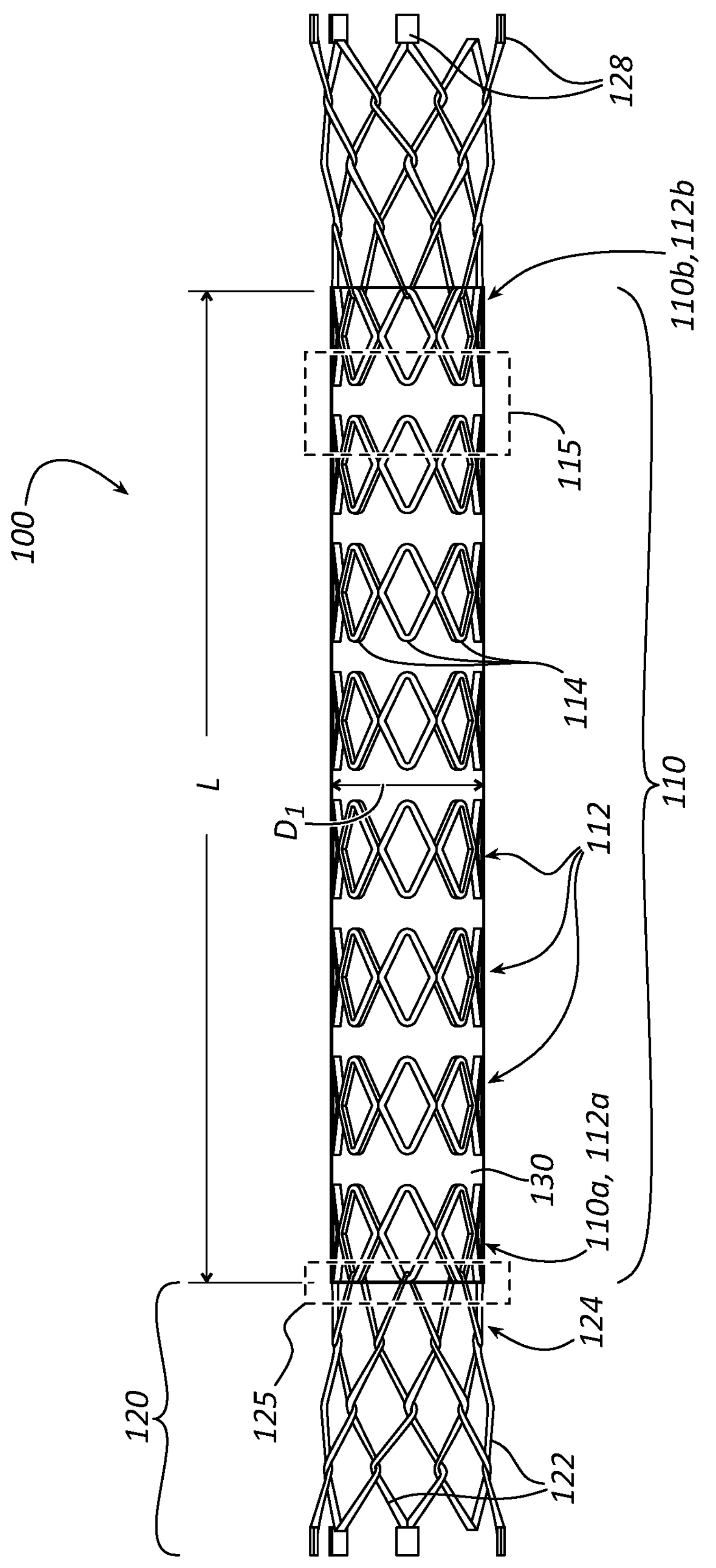
FIG. 2A illustrates a side-on view of an intraluminal prosthesis in accordance with some embodiments.
Figure 2B:
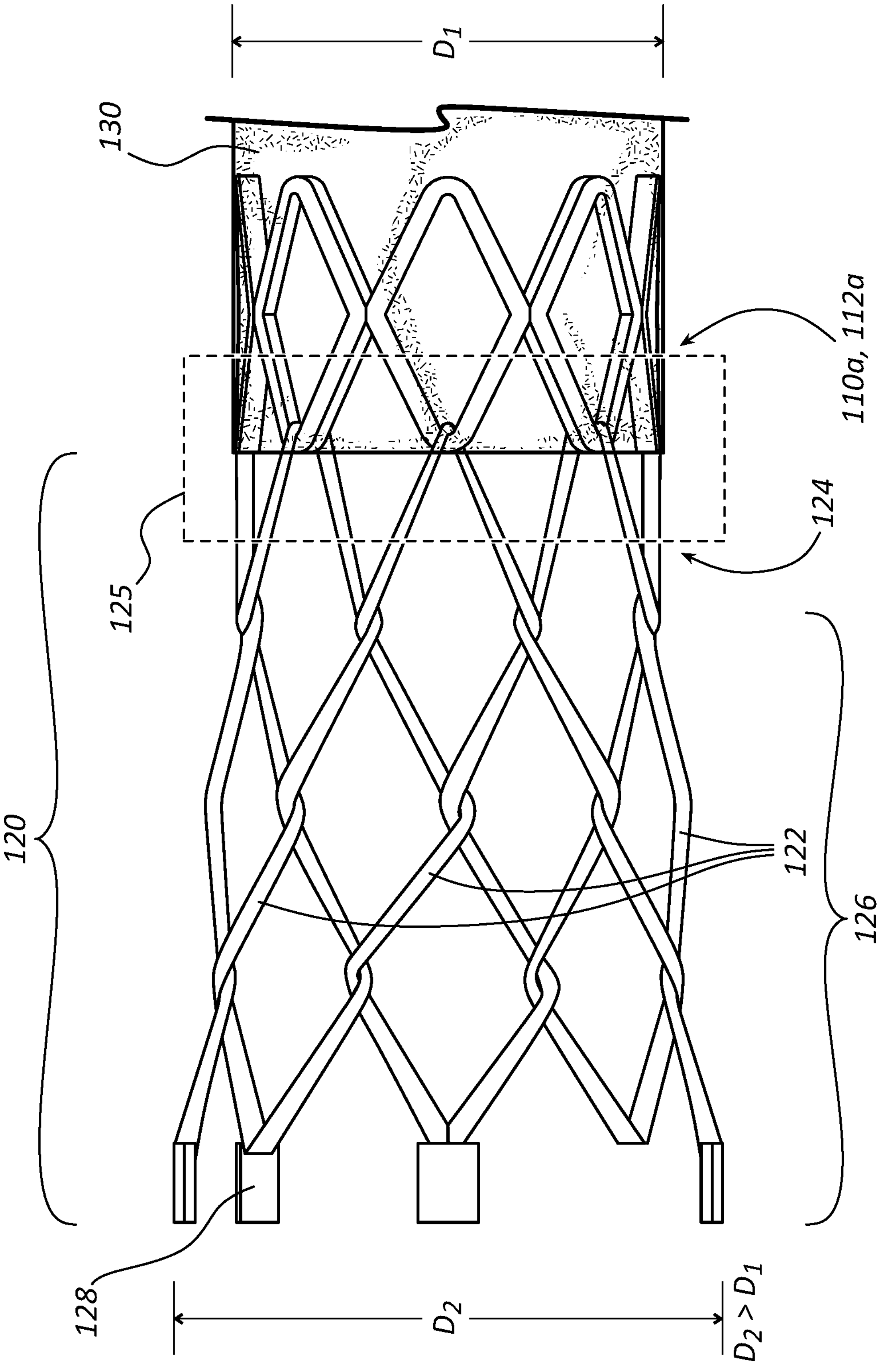
FIG. 2B illustrates a close-up view of the intraluminal prosthesis of FIG. 2A about a coupling between a terminal frame and an annular member of a main frame of the intraluminal prosthesis.
Figure 3:
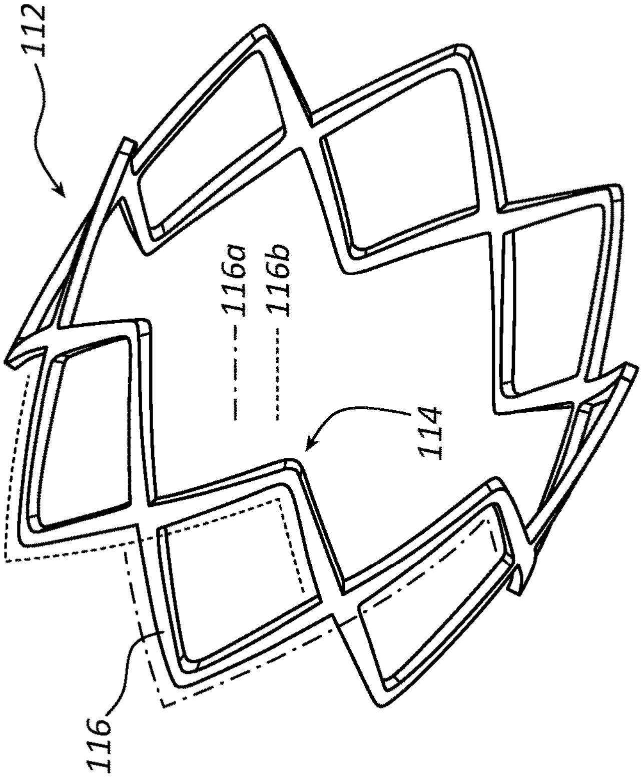
FIG. 3 illustrates an annular member of a main frame of an intraluminal prosthesis in accordance with some embodiments.
Figure 4:
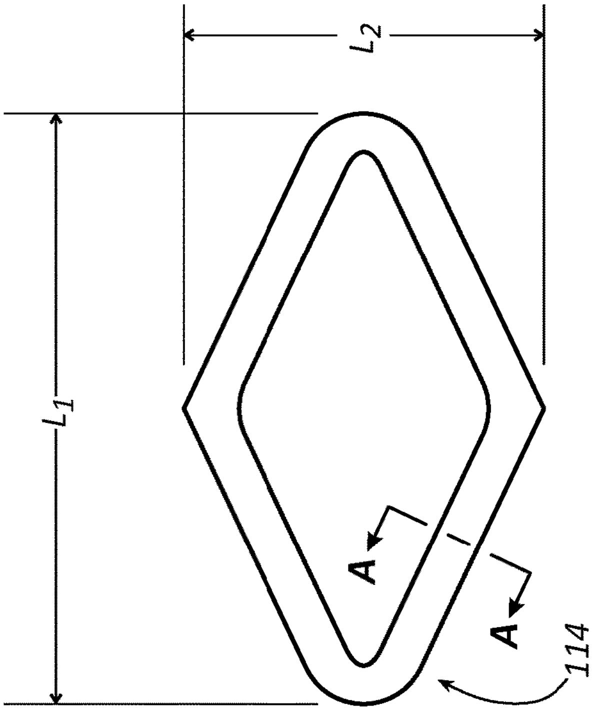
FIG. 4 illustrates a diamond-shaped cell of an annular member of a main frame of an intraluminal prosthesis in accordance with some embodiments.
Figure 5:
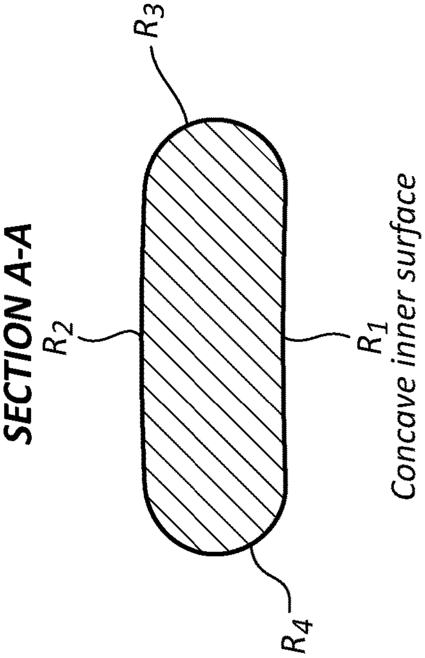
FIG. 5 illustrates a cross section of a strut of an annular member of a main frame of an intraluminal prosthesis in accordance with some embodiments.

FIG. 2A illustrates a side-on view of the intraluminal prosthesis 100 in accordance with some embodiments, while FIG. 2B illustrates a close-up view of the intraluminal prosthesis 100 about a woven coupling 125 between a terminal frame 120 and an annular member 112 of a main frame 110 of the intraluminal prosthesis 100. FIG. 3 illustrates the annular member 112 of the main frame 110 in accordance with some embodiments. FIG. 4 illustrates a diamond-shaped cell 114 of the annular member 112 in accordance with some embodiments. FIG. 5 illustrates a cross section of a strut 116 of the annular member 112 in accordance with some embodiments.

As shown in FIGS. 2A and 2B, the intraluminal prosthesis 100 includes a mixed frame of the main frame 110 and the terminal frame 120, as well as a tubular graft 130 over the main frame 110, each of which is described in further detail herein. While not shown in FIGS. 2A and 2B, the intraluminal prosthesis 100 includes an insertion state or compressed state for advancing the intraluminal prosthesis 100 through a patient's vasculature to the portal vein PV. The intraluminal prosthesis 100 also includes an expanded state for placing the intraluminal prosthesis 100 in the portal vein PV. The intraluminal prosthesis 100 can be self-expanding in that it can expand, by itself, from the insertion state to the expanded state.

The main frame 110 includes or is formed of a number of annular members 112, for example, of nitinol that are longitudinally spaced apart from each other. For example, a first-end annular member 112*a* is at a first end 110*a* of the main frame 110, while a second-end annular member 112*b* is at a second end 110*b* of the main frame 110.

Each annular member 112 includes a number of diamond-shaped cells 114, one of which is shown in FIG. 4. The diamond-shaped cells 114 can vary with respect to their major dimension $L_1$ and minor dimension $L_2$. In the annular member 112 shown in FIG. 3, the diamond-shaped cells 114 are joined to together by their vertices along the minor dimension $L_2$ to form the annular member 112. The longitudinal spacing of the annular members 112 in the main frame 110 is determined, in part, by the major dimension $L_1$ or minor dimension $L_2$ of the diamond-shaped cells 114 depending upon which dimension is longitudinal with the intraluminal prosthesis 100.

Each annular member 112 also includes a number of 'S'-shaped struts 116 forming the diamond-shaped cells 114. As shown in FIG. 5, each 'S'-shaped strut 116 includes a cross-sectional shape bounded by two parallel arcs R1 and R2 and two polynomial curves R3 and R4. The parallel arc R2 provide a concave outer surface and the parallel arc R1 provides a concave inner surface for each 'S'-shaped strut 116. The concave outer surface of the 'S'-shaped struts 116 provides as much surface as possible for contact with the luminal surface of the portal vein PV.

With respect to the 'S'-shaped struts 116 forming the diamond-shaped cells 114, a first 'S'-shaped strut 116*a* is joined at its midpoint and tail respectively to a head and midpoint of a second 'S'-shaped strut 116*b* to form the diamond-shaped cell 114 therebetween. Joining a number of such 'S'-shaped struts 116 in the foregoing fashion yields the number of diamond-shaped cells 114 shown for the annular member 112 of FIG. 3. Again, the diamond-shaped cells 114 can vary with their major dimension $L_1$ and minor dimension $L_2$. This is in accordance with the degree to which the 'S'-shaped struts 116 are compressed or elongated. For example, relatively compressed 'S'-shaped struts 116 can provide the diamond-shaped cell 114 of FIG. 4, in which the major dimension $L_1$ of the diamond-shaped cell 114 is greater than the minor dimension $L_2$ of the diamond-shaped cell 114.

The terminal frame 120 includes or is formed of woven struts 122, for example, of nitinol. The terminal frame 120 includes a coupled end 124 and an uncoupled end portion 126 opposite the coupled end 124 that enables long-term placement of the intraluminal prosthesis 100 in the portal vein PV without shifting. The coupled end 124 of the terminal frame 120 is wovenly coupled to at least one of the first-end annular member 112*a* or the second-end annular member 112*b* in the woven coupling 125 respectively at the first end 110*a* or the second end 110*b* of the main frame 110. The woven coupling 125 is an extension of the woven struts 122 into the first-end annular member 112*a* or the second-end annular member 112*b*, which maintains flexibility in the intraluminal prosthesis 100 while providing collapse-preventing strength to the intraluminal prosthesis 100. When a second terminal frame 120 is present in the intraluminal prosthesis 100 as shown in FIG. 2A, the second terminal frame 120 of the pair of terminal frames 120 is wovenly coupled to the other of the first-end annular member 112*a* or the second-end annular member 112*b*. The second terminal frame 120 can be the same as the first terminal frame 120 or different with respect to, for example, axial length or conicity. Regardless, having two terminal frames 120 without the tubular graft 130 prevents "capping" of the portal vein PV when the intraluminal prosthesis 100 is placed therein.

The uncoupled end portion 126 of the terminal frame 120 has a diameter greater than a diameter of both the main frame 110 and the coupled end 124 of the terminal frame 120 in the insertion state or the expanded state of the intraluminal prosthesis 100. The uncoupled end portion 126 of the terminal frame 120 can include a number of radiodense keys 128 such as tantalum keys 128 capping the woven struts 122 or fixing ends of the woven struts 122 together. The number of tantalum keys 128 can be an odd number of tantalum keys 128 greater than unity such as three, five, seven, or nine tantalum keys 128. Each tantalum key 128 has a width greater than a width of any one of the woven struts 122 it caps. This facilitates identification of the tantalum keys 128 by radiographic methods such as fluoroscopy. When a second terminal frame 120 is present in the intraluminal prosthesis 100 as shown in FIG. 2A, the second terminal frame 120 of the pair of terminal frames 120 can include the tantalum keys 128 as well, thereby allowing the clinician to improve positioning of the intraluminal prosthesis 100 by the radiographic methods.

The tubular graft 130 is over at least a majority of the main frame 110, under the majority of the main frame 110, or the majority of the main frame 110 is sandwiched between a pair of concentric tubular grafts 130. Any embodiment of the foregoing tubular graft 130 can extend from the first-end annular member 112*a* to the second-end annular member 112*b* such as up to the vertices of the diamond-shaped cells 114, up to the woven coupling 125, or past the woven coupling 125 and up to a portion of the coupled end 124 of the terminal frame 120.

Any two adjacent annular members 112 are flexibly coupled together solely by a flexible coupling 115 provided by the tubular graft 130 between the two adjacent annular members 112 as shown in FIGS. 2A and 2B. Such adjacent annular members 112 fixedly attached to the tubular graft 130 but are otherwise physically separate from each other or unconnected. A number of flexible couplings 115 between the annular members 112 imparts flexibility to the main frame 110 about the annular members 112. The flexible couplings 115 about the annular members 112 enable the intraluminal prosthesis 100 to keep a same length whether the intraluminal prosthesis 100 is in the insertion state or the expanded state. A relatively high degree of flexibility accommodates movement of surrounding liver tissue with little to no fatigue-based damage to the intraluminal prosthesis 100, little to no permanent deformation of the intraluminal prosthesis 100, or little to no change in cross-sectional area of the intraluminal prosthesis 100.

The tubular graft 130 can be a medically acceptable polymer such high-density polyethylene ("HDPE") or expanded polytetrafluorethylene ("ePTFE"). Such a tubular graft 130 prevents tissue ingrowth about the main frame 110, thereby maintaining the flexibility of the main frame 110.

Adverting back the main frame 110 in view of the foregoing description, a length L of the main frame 110 is satisfied by Equation 1:

$$L=ML_1+(M-1)S \quad \text{(Equation 1)},$$

wherein M is the number of annular members 112, $L_1$ is a major dimension of the diamond-shaped cells 114, and S is determined in accordance with Equation 2:

$$S=\sqrt{L_1^2+L_2^2}-L_1 \quad \text{(Equation 2)},$$

wherein $L_2$ is a minor dimension of the diamond-shaped cells 114 determined in accordance with Equation 3:

$$L_2=\pi D_1/N \quad \text{(Equation 3)},$$

and wherein $D_1$ is a diameter of the main frame 110 in the insertion state or the expanded state of the intraluminal prosthesis 100 and N is the number of diamond-shaped cells 114 in each annular member 112.

Figure 6A:
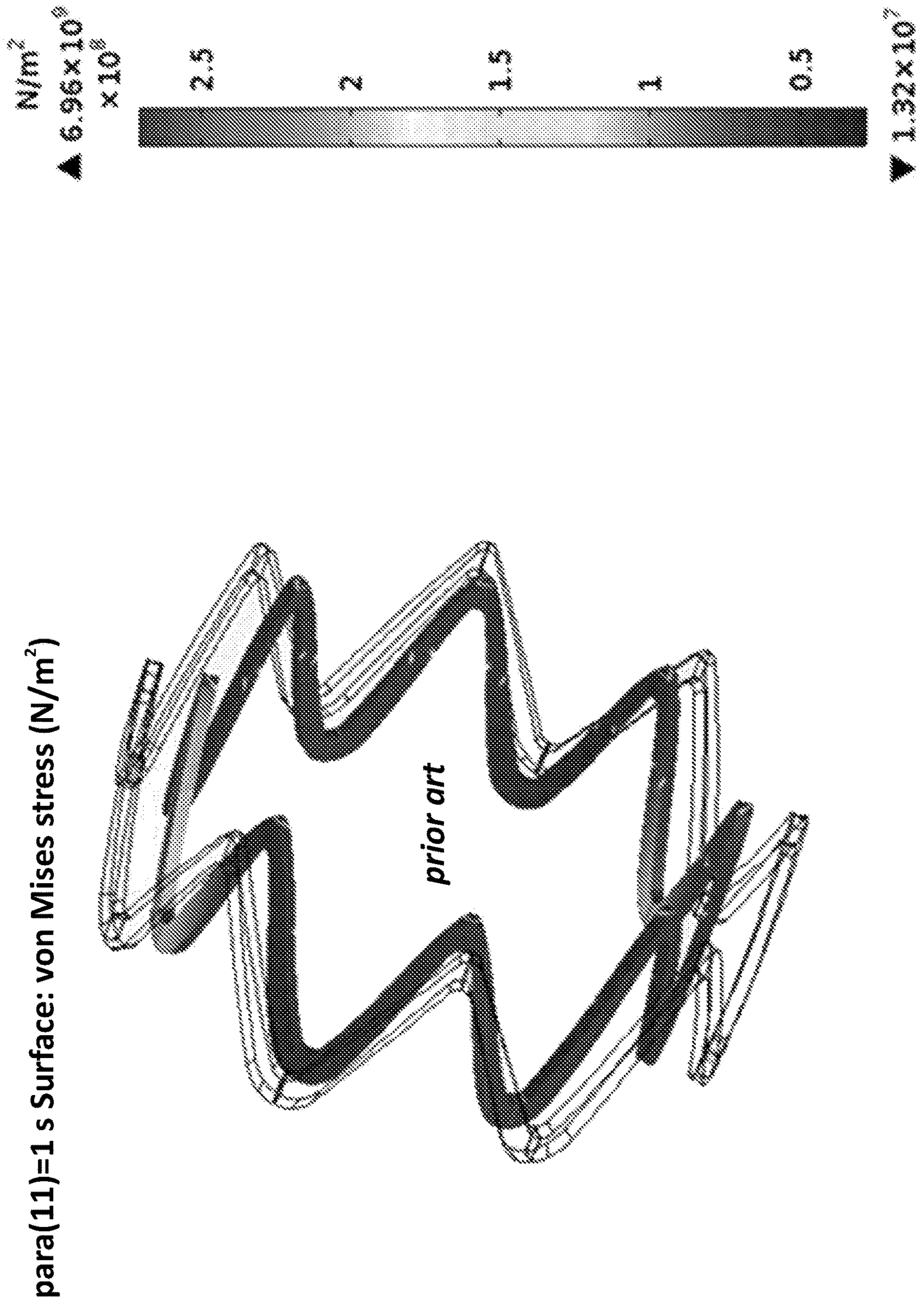
FIG. 6A illustrates stress distribution in an annular member of a prior-art intraluminal prosthesis.
Figure 6B:
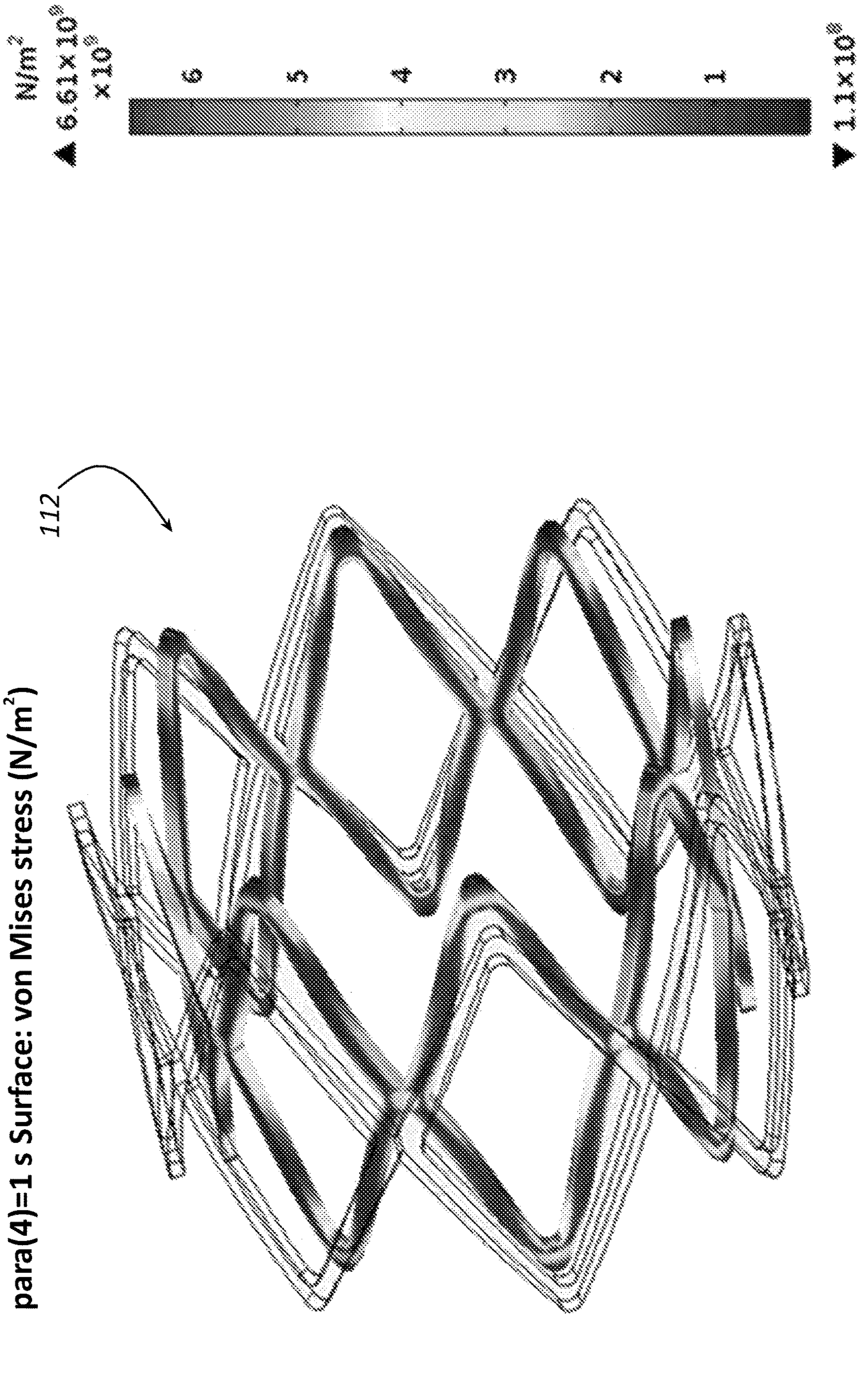
FIG. 6B illustrates stress distribution in an annular member of an intraluminal prosthesis in accordance with some embodiments.

FIG. 6A illustrates stress distribution in an annular member of a prior-art intraluminal prosthesis, whereas FIG. 6B illustrates stress distribution in the annular member 112 of the intraluminal prosthesis 100 in accordance with some embodiments. As shown, the prior-art annular member experiences a greater stress over the entire prior-art annular member than the annular member 112 when a radial resistive force is applied to reduce the diameter of each annular member by 1 mm.

Figure 7A:
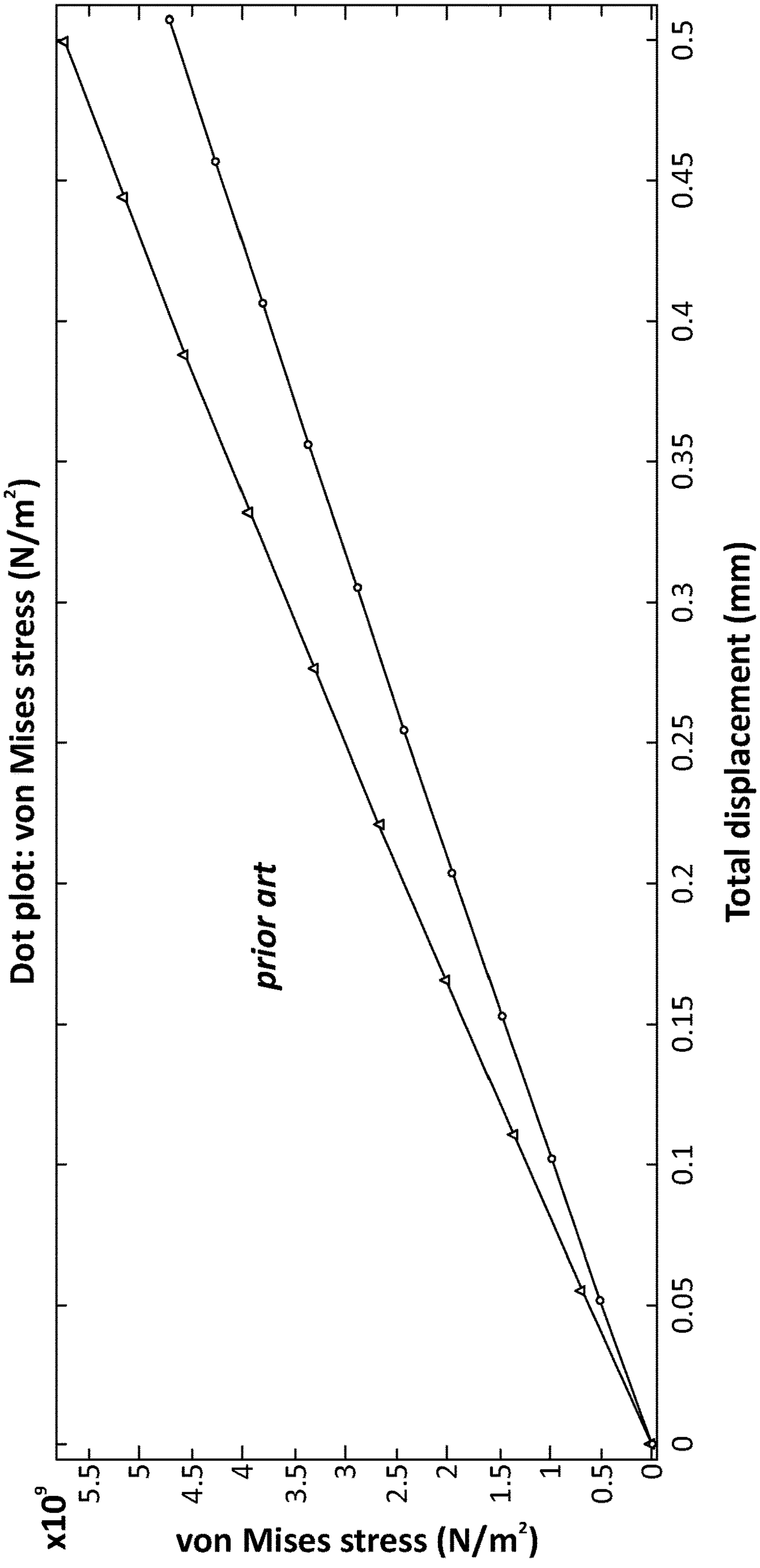
FIG. 7A illustrates a plot of von Mises stress as a function of displacement in the prior-art annular member.
Figure 7B:
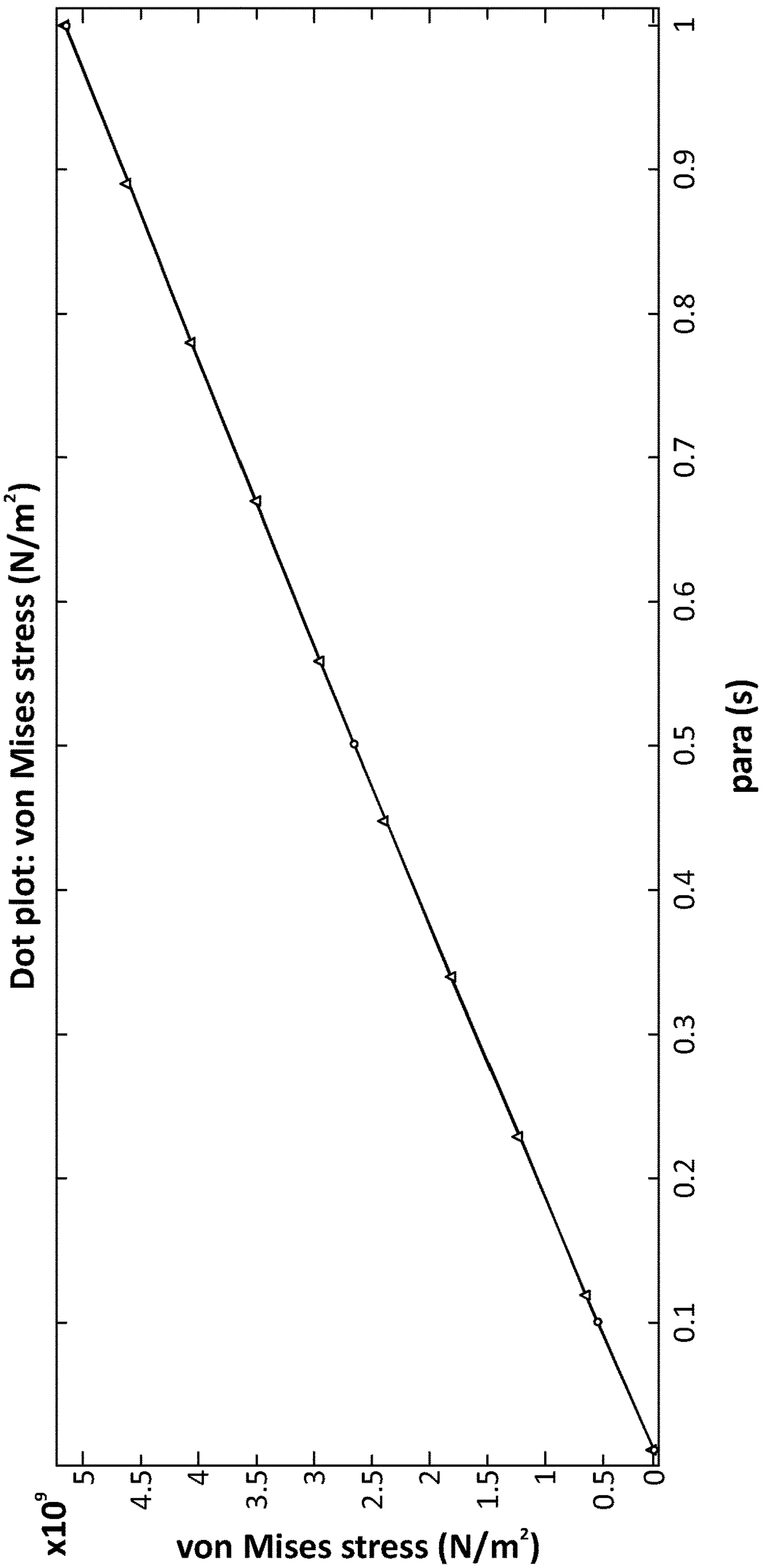
FIG. 7B illustrates a plot of von Mises stress as a function of displacement in the annular member in accordance with some embodiments.

FIG. 7A illustrates a plot of von Mises stress as a function of displacement in the prior-art annular member, whereas FIG. 7B illustrates a plot of von Mises stress as a function of displacement in the annular member 112 in accordance with some embodiments. As shown, the prior-art annular member experiences different stresses at each end of the prior-art annular member, whereas the annular member 112 experiences the same stress at each end of the annular member 112.

Figure 8A:
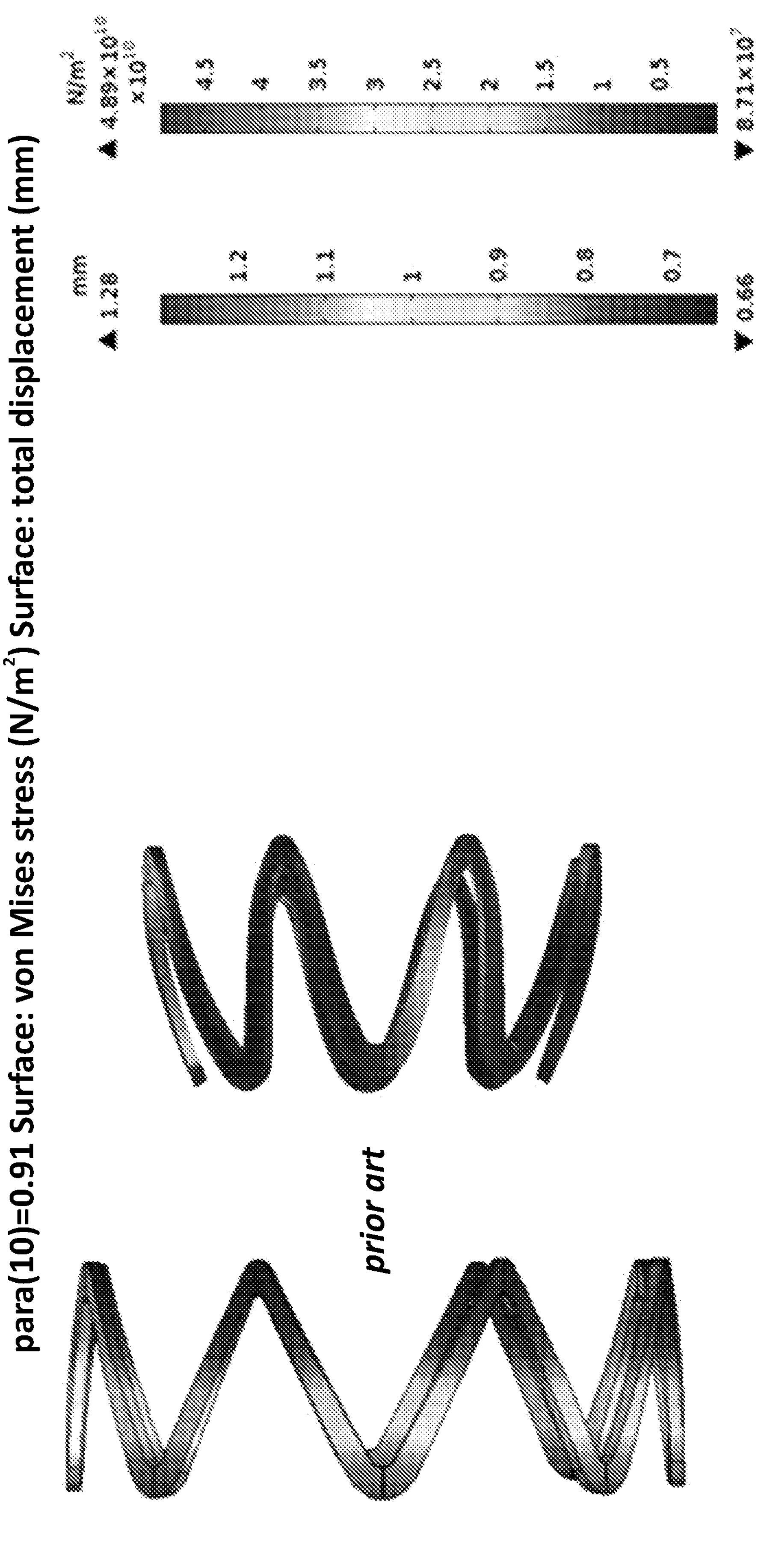
FIG. 8A illustrates stress distribution and displacement in the prior-art annular member.
Figure 8B:
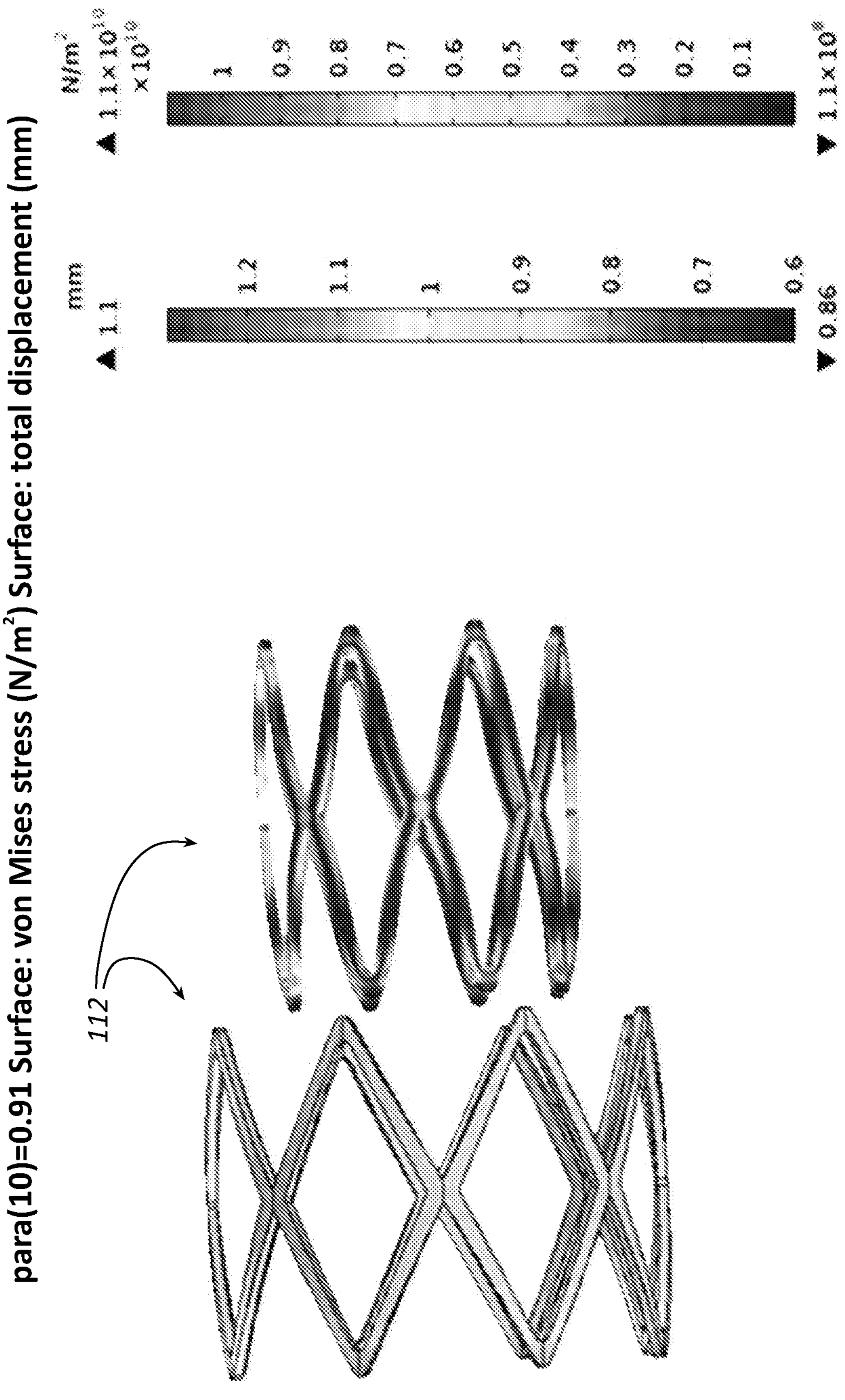
FIG. 8B illustrates stress distribution and displacement in the annular member in accordance with some embodiments.
Figure 9A:
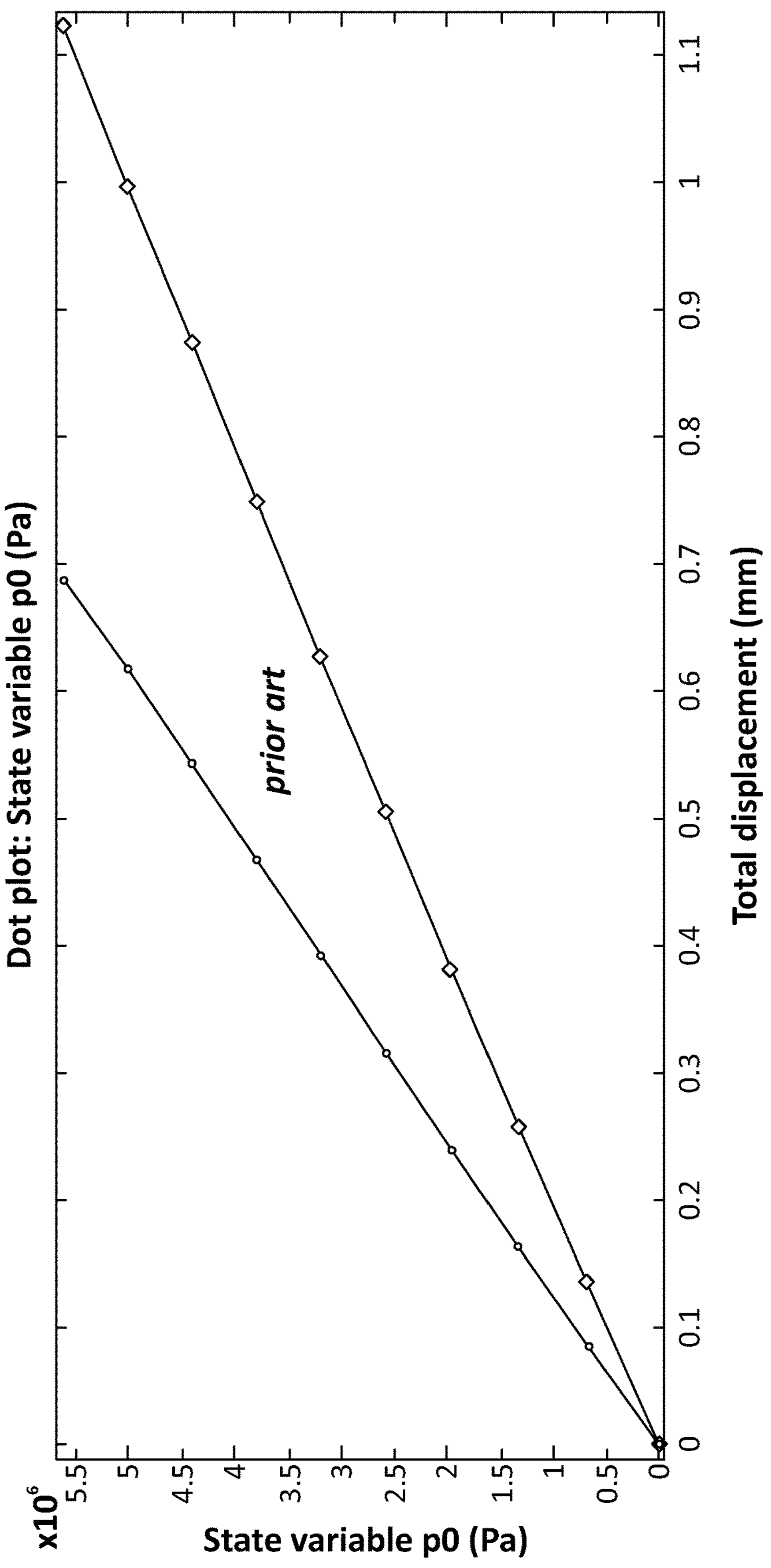
FIG. 9A illustrates a plot of a state variable as a function of displacement for the prior-art annular member.
Figure 9B:
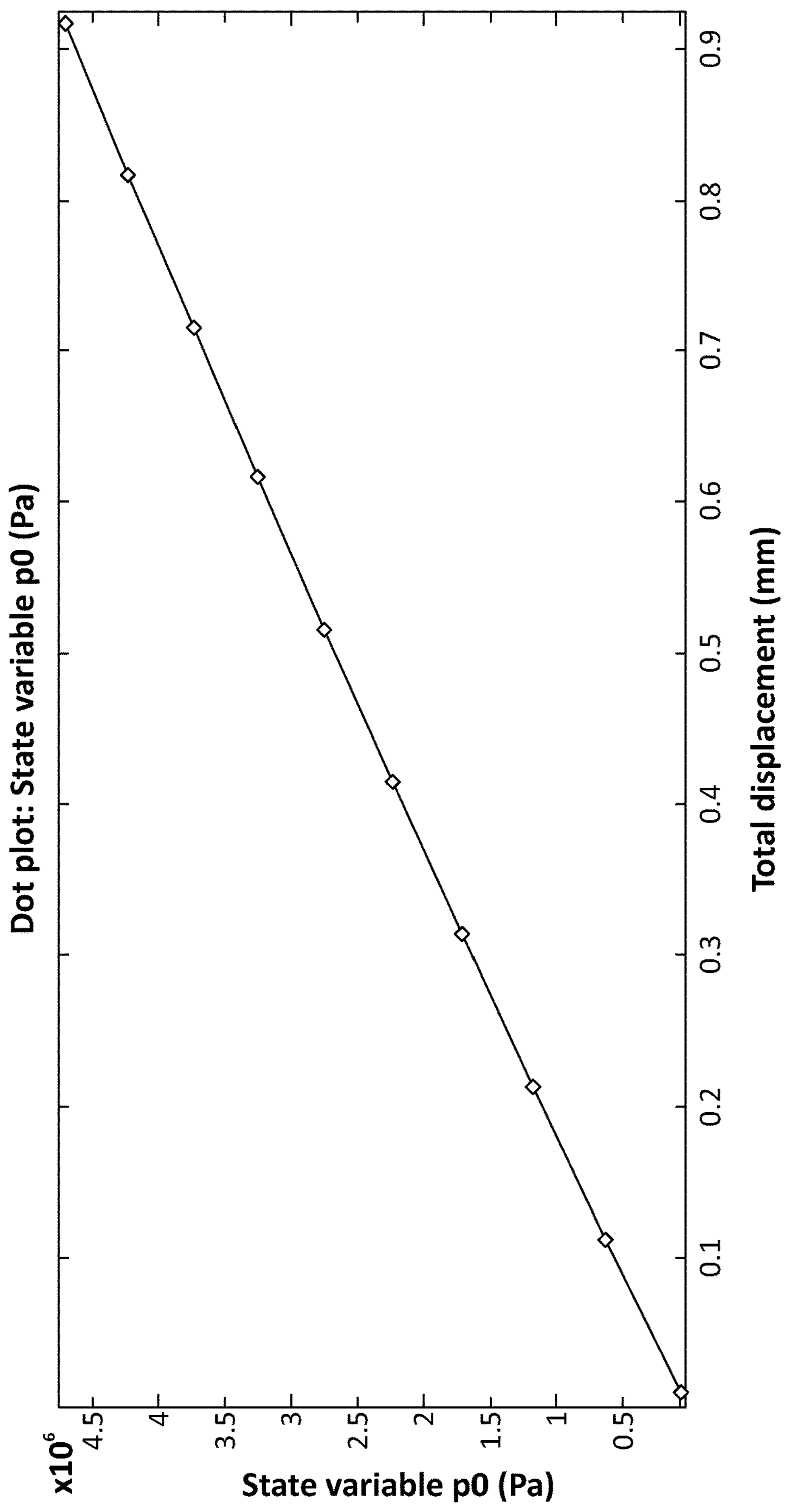
FIG. 9B illustrates a plot of a state variable as a function of displacement for the annular member in accordance with some embodiments.

FIG. 8A illustrates stress distribution and displacement in the prior-art annular member when placing a radial load thereon, whereas FIG. 8B illustrates stress distribution and displacement for the annular member 112 under the same radial load in accordance with some embodiments. In addition, FIG. 9A illustrates a plot of a state variable p0 as a function of displacement for the prior-art annular member under the foregoing radial load, whereas FIG. 9B illustrates a plot of the state variable p0 as a function of displacement for the annular member 112 under the foregoing radial load in accordance with some embodiments. As shown, the prior-art annular member moves through different radial distances at each end of the prior-art annular member, whereas the annular member 112 moves through similar radial distances at each end of the annular member 112.

A method for producing the mixed-frame intraluminal prosthesis 100 includes forming the main frame 110 of the mixed frame by fixedly attaching the physically separate annular members 112 to the tubular graft 130; forming a pair of terminal frames 120 of the mixed frame shown in FIGS. 2A and 2B by weaving a first set of struts 122 to the first-end annular member 112*a* at the first end 110*a* of the main frame 110 to form a first terminal frame 120 and weaving a second set of struts 122 to the second-end annular member 112*b* at the second end 110*b* of the main frame 110 to form a second terminal frame 120; and fixing ends of each set of struts 122 together with the tantalum keys 128, which make the intraluminal prosthesis 100 suitable for identification by radiographic methods.

The method further can further include longitudinally arranging each annular member 112 relative to a previous annular member 112 before attachment to the tubular graft 130 when forming the main frame 100, thereby ensuring flexibility of the flexible couplings 115 between the annular members 112 provided by the tubular graft 130.

Fixedly attaching the annular members 122 to the tubular graft 130 includes inserting the annular members 122 into the tubular graft 130 before attachment to the tubular graft 130 or sandwiching the annular members 122 between the tubular graft 130 and another tubular graft 130 before attachment to either tubular graft 130.

Fixing the ends of each set of struts 122 together with the tantalum keys 128 includes fixing the ends of each set of struts 122 together such that an odd number of tantalum keys 128 result.

The method can further include fixing any remaining ends of each set of struts 122 together without the tantalum keys 128 to satisfy the odd number of tantalum keys 128.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An intraluminal prosthesis having an insertion state and an expanded state, the intraluminal prosthesis comprising:

a main frame including a plurality of physically separate annular members, each annular member including a plurality of diamond-shaped cells, a terminal frame including woven struts, the terminal frame including a coupled end coupled to at least one of a first-end annular member or a second-end annular member respectively at a first end or a second end of the main frame; and a tubular graft over the main frame, the tubular graft extending from the first-end annular member to the second-end annular member.

2. The intraluminal prosthesis of claim 1, wherein the terminal frame includes an uncoupled end portion opposite the coupled end, the uncoupled end portion having a diameter greater than a diameter of the main frame in the expanded state of the intraluminal prosthesis.

3. The intraluminal prosthesis of claim 2, wherein the uncoupled end portion includes an odd number of tantalum keys capping the woven struts, the tantalum keys having a width greater than that of the woven struts to facilitate identification of the tantalum keys by radiographic methods.

4. The intraluminal prosthesis of claim 1, wherein each annular member includes a plurality of 'S'-shaped struts forming the plurality of diamond-shaped cells, each 'S'-shaped strut including a cross-sectional shape bounded by two parallel arcs and two polynomial curves.

5. The intraluminal prosthesis of claim 1, wherein any two adjacent annular members are coupled together solely by a flexible coupling provided by the tubular graft over the two adjacent annular members.

6. The intraluminal prosthesis of claim 5, wherein the flexible coupling about the any two adjacent annular members enables the intraluminal prosthesis to keep a same length whether the intraluminal prosthesis is in the insertion state or the expanded state.

7. The intraluminal prosthesis of claim 5, wherein the flexible coupling imparts flexibility to the main frame about the any two adjacent annular members.

8. The intraluminal prosthesis of claim 7, wherein the tubular graft prevents tissue ingrowth about the main frame, thereby maintaining the flexibility of the main frame.

9. The intraluminal prosthesis of claim 1, wherein the tubular graft is high-density polyethylene ("HDPE") or expanded polytetrafluorethylene ("ePTFE").

10. The intraluminal prosthesis of claim 1, wherein both the main frame and the terminal frame are nitinol.

11. An intraluminal prosthesis having a mixed frame, the intraluminal prosthesis comprising:

a main frame of the mixed frame including a number of physically separate annular members, each annular member including a number of 'S'-shaped struts forming a number of diamond-shaped cells, a pair of terminal frames of the mixed frame including woven struts, each terminal frame including a coupled end exclusively coupled to one of a first-end annular member or a second-end annular member respectively at a first end or a second end of the main frame; and a tubular graft over the main frame, the tubular graft extending from the first-end annular member to the second-end annular member.

12. The intraluminal prosthesis of claim 11, wherein each terminal frame includes an uncoupled end portion opposite the coupled end, the uncoupled end portion including an odd number of tantalum keys capping the woven struts, the tantalum keys having a width greater than that of the woven struts to facilitate identification of the tantalum keys by radiographic methods.

13. The intraluminal prosthesis of claim 11, wherein any two adjacent annular members are coupled together solely by a flexible coupling provided by the tubular graft over the two adjacent annular members.

14. The intraluminal prosthesis of claim 11, wherein the tubular graft is high-density polyethylene ("HDPE") configured to prevent tissue ingrowth about the main frame, thereby maintaining flexibility in the main frame about the annular members.

15. The intraluminal prosthesis of claim 11, wherein a length L of the main frame is satisfied by Equation 1:

$$L=ML_1+(M-1)S \quad \text{(Equation 1)},$$

wherein M is the number of annular members, $L_1$ is a major dimension of the diamond-shaped cells, and S is determined in accordance with Equation 2:

$$S=\sqrt{L_1^2+L_2^2}-L_1 \quad \text{(Equation 2)},$$

wherein $L_2$ is a minor dimension of the diamond-shaped cells determined in accordance with Equation 3:

$$L_2=\pi D_1/N \quad \text{(Equation 3)},$$

and wherein $D_1$ is a diameter of the main frame in an insertion state or an expanded state of the intraluminal prosthesis and N is the number of diamond-shaped cells in each annular member.

16. A method for a mixed-frame intraluminal prosthesis, comprising:

forming a main frame of the mixed-frame intraluminal prosthesis by fixedly attaching a number of physically separate annular members to a tubular graft, each annular member including a number of 'S'-shaped struts forming a number of diamond-shaped cells;

forming a pair of terminal frames of the mixed-frame intraluminal prosthesis by weaving a first set of struts to a first-end annular member at a first end of the main frame to form a first terminal frame and weaving a second set of struts to a second-end annular member at a second end of the main frame to form a second terminal frame; and fixing ends of each set of struts together with tantalum keys suitable for identification thereof by radiographic methods.

17. The method of claim 16, further comprising:

longitudinally arranging each annular member relative to a previous annular member before attachment to the tubular graft when forming the main frame, thereby ensuring flexibility of flexible couplings between annular members provided by the tubular graft.

18. The method of claim 16, wherein fixedly attaching the annular members to the tubular graft includes inserting the annular members into the tubular graft before attachment to the tubular graft or sandwiching the annular members between the tubular graft and another tubular graft before attachment to either tubular graft.

19. The method of claim 16, wherein fixing the ends of each set of struts together with the tantalum keys includes fixing the ends of each set of struts together such that an odd number of tantalum keys result.

20. The method of claim 19, further comprising fixing any remaining ends of each set of struts together without the tantalum keys to satisfy the odd number of tantalum keys.

* * * * *